(12) United States Patent
Ozelkan et al.

(10) Patent No.: US 6,524,604 B1
(45) Date of Patent: Feb. 25, 2003

(54) METHOD, COMPOSITION AND KIT TO REMOVE LICE OVA FROM THE HAIR

(75) Inventors: Serap Ozelkan, Plainview, NY (US); Zegong Zhang, Stony Brook, NY (US); Vyacheslav Malayev, Jamaica, NY (US)

(73) Assignee: Del Laboratories, Inc., Farmingdale, NY (US)

( * ) Notice: Subject to any disclaimer, the term of this patent is extended or adjusted under 35 U.S.C. 154(b) by 0 days.

(21) Appl. No.: 09/621,255

(22) Filed: Jul. 21, 2000

(51) Int. Cl.[7] ............................................... A01N 25/04
(52) U.S. Cl. ...................... 424/406; 424/405; 424/407; 424/70.1; 424/601; 514/469; 514/470; 514/558; 514/574; 514/578
(58) Field of Search ................................ 424/405, 70.1, 424/406, 407, 409, 601; 514/469, 470, 557, 558, 574, 578; 549/200, 203, 205

(56) References Cited

U.S. PATENT DOCUMENTS

| | | | |
|---|---|---|---|
| 4,126,700 A | 11/1978 | Lover et al. | |
| 4,518,593 A | 5/1985 | Juvin et al. | |
| 4,927,813 A | 5/1990 | Bernstein | |
| 5,543,085 A * | 8/1996 | Miner | ........................ 510/118 |
| 5,547,665 A | 8/1996 | Upton | |
| 5,858,383 A | 1/1999 | Precopio | |
| 5,965,603 A * | 10/1999 | Johnson et al. | ............. 514/450 |
| 6,006,758 A | 12/1999 | Thorne | |
| 6,103,248 A * | 8/2000 | Burkhart et al. | ............. 424/401 |
| 6,120,779 A * | 9/2000 | Nayak et al. | ............... 424/401 |
| 6,136,838 A * | 10/2000 | Chern et al. | ................. 514/404 |
| 6,162,419 A * | 12/2000 | Perricone et al. | ............. 424/59 |
| 6,231,837 B1 * | 5/2001 | Stroud et al. | ................. 424/59 |

OTHER PUBLICATIONS

Taplin et al., *Journal of the American Medical Association*, vol. 247, No. 22, pp. 3103–3105 (1982).

* cited by examiner

Primary Examiner—Neil S. Levy
(74) Attorney, Agent, or Firm—Kirschstein, et al.

(57) ABSTRACT

A composition for removal of lice ova or nits from the hair of human subjects comprises about 1–50% by weight of dimethylisosorbide (DMI) in an aqueous vehicle having a neutral to acidic pH. The composition is preferably in the form of a gel or a liquid shampoo, the shampoo preferably including an active pediculicidal or ovicidal agent. A method of removing lice ova from human hair comprises the application of the novel composition to the hair and subsequent removal thereof, e.g., by rinsing with water. Any unremoved ova can be physically dislodged by combing. The composition can also be included with a fine tooth nit comb in a kit for removal of lice ova from human hair.

10 Claims, 1 Drawing Sheet

METHOD, COMPOSITION AND KIT TO REMOVE LICE OVA FROM THE HAIR

BACKGROUND OF THE INVENTION

1. Field of the Invention

The present invention relates to methods and compositions for the loosening and subsequent removal of lice egg infestations from the hair and scalp.

2. Description of the Prior Art

Throughout history, human beings in all parts of the world have suffered from parasitical infestations, including infestations of the hair and scalp by head lice (*Pediculus humanus var capitis*). Many methods of treating such head louse infestations have been proposed and utilized for centuries including, for example, washing the head with strong soaps and lye and the utilization of kerosene to kill adult lice and their ova. In more recent times, various ectoparasiticides have been incorporated into creams, gels, shampoos and the like for application to human hair and scalp.

Some of the ectoparasiticides which have been utilized as pediculicidal treatments since the early 1950s and are commercially available today in various forms include the insecticides lindane and malathion, as well as pyrethrins (chrysanthemin carboxylic esters of pyrethrolone), derived from certain variants of the chrysanthemum family. Compositions containing pyrethrins as active ingredients normally include, in addition, a pyrethrin synergist such as piperonyl butoxide which greatly enhances pediculicidal activity. See, generally, Journal of the American Medical Association, Vol. 247, No. 22, pp. 3103–05 (Jun. 11, 1982), for a description of various pediculicidal agents and compositions.

One of the serious drawbacks of the commonly utilized compositions for treatment of head louse infestations is that while many of them are highly effective against the adult parasites, and some produce significant mortality rates among louse ova as well, they leave a substantial number of ova intact after treatment. These lice eggs or nits cling tenaciously to the hair shafts, usually close to the scalp, because they are surrounded by a layer of chitinous material that acts as a "nit cement." If they are not physically removed from the subject's hair, they may simply hatch after a period of time and cause re-infestation.

Among the techniques conventionally used to remove the lice eggs after treatment of a subject's hair and scalp with pediculicidal agents are the vigorous brushing of the hair, combing with a fine tooth nit comb or the use of implements such as tweezers, pencils or sharpened sticks to remove the nits individually from the hair shafts, usually with the aid of a bright light and some form of optical magnification. These techniques are time-consuming, inefficient and rarely succeed in removing substantially all of the remaining lice eggs because they are firmly adhered by the cement to the hair.

Lice ova removal or loosening compositions to be applied to the hair have been proposed in the prior art. For example, U.S. Pat. No. 5,557,665 discloses the application of an enzyme composition to the hair, said composition comprising a water-based enzyme and a stabilizer. The enzyme causes the swelling and/or breakdown of the nit cement to facilitate the subsequent removal of the nits from the hair. Such enzyme compositions are, however, relatively difficult to manufacture and are expensive for consumers, who are frequently non-wealthy parents of young children. Moreover, it is not clear that such compositions are substantially more effective than the physical removal techniques that have been practiced traditionally in the prior art.

Hence, there is a need for improved compositions and methods to remove lice ova from the hair and scalp of an infested subject.

SUMMARY OF THE INVENTION

1. Objects of the Invention

It is an object of the present invention to provide compositions which may be applied to the hair and scalp of human subjects, or to other hairy body areas, and which are effective in loosening and removing lice ova or nits therefrom.

An additional object of the present invention is to provide compositions as described above which are safe, easy to use and relatively inexpensive.

A further object of the present invention is to provide compositions as described which are not enzyme based.

Yet another object of the present invention is to provide compositions as described above which also include active pediculicidal and/or ovicidal ingredients.

Still another object of the present invention is to provide a method of loosening lice ova from the hair of a human subject by applying compositions as described above.

Yet a further object of the present invention is to provide a kit that can be used to perform the method of the invention.

2. Brief Description of the Invention

In keeping with these objects and others which will become apparent hereinafter, the present invention resides, in a first aspect, in compositions for removal of lice ova or nits from the hair of human subjects. The novel nit removal compositions comprise from about 1 to about 50% by weight of dimethyl isosorbide in an aqueous vehicle having a neutral to acidic pH. The compositions can be in any suitable physical form, but are preferably in the form of a gel or liquid.

The phrase "% by weight" used throughout this specification and the appended claims refers to the percentage of the weight of the total composition constituted by the specified component or ingredient.

The invention also comprehends in a second aspect a method of loosening lice ova from the hair or scalp of a human subject, or from other hair/body areas, by applying compositions as described above to the hair or scalp of the subject and subsequently rinsing off with water, with the remaining nits being combed out with a fine tooth comb.

In a third aspect, the invention comprehends kits for use in practicing the method of the invention, said kits containing a composition according to the invention and a nit comb.

DETAILED DESCRIPTION OF THE INVENTION

Figure 1:
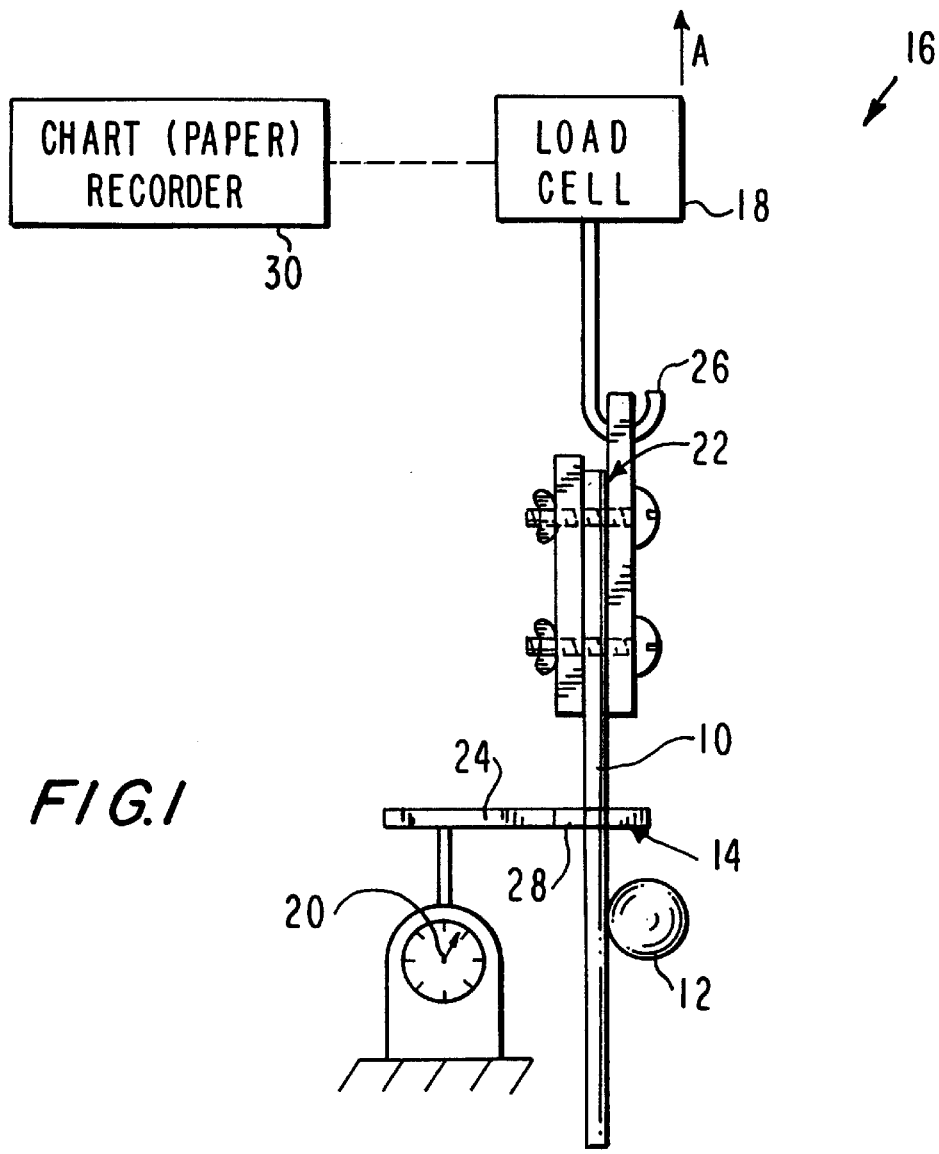
FIG. 1 is a diagram of the test setup whereby the force required to dislodge a nit from a human hair strand with a nit comb was measured.

Dimethyl isosorbide (DMI), also known by the Chemical Abstracts name 1,4:3,6 dianhydro-2,5-di-o-methyl-D-glucitol, is a chemically inert, high-boiling point vehicle or surfactant which is water and oil-soluble. It is highly safe and non-toxic, has a pleasant feel and good spreadability and has been used in such topical products as sunscreens, antibiotic and corticosteroid ointments and mineral oil lotions. One commercial DMI product is supplied by ICI Americas Inc. in the form of a water white liquid marketed under the trade name ARLASOLVE®. ARLASOLVE® has excellent pH stability, having been observed in water over a pH range of 2–10 for a month with no apparent change.

It has now been discovered unexpectedly that DMI is effective in loosening and dislodging louse ova or nits from hair shafts. DMI formulated as a thickened gel or in a shampoo base, whether at a neutral or acidic pH, has been found in extensive in vitro studies to have good nit-loosening utility.

Accordingly, the compositions of the invention comprise from about 1 to about 50% by weight, and preferably from about 5 to about 25% by weight, of DMI in an aqueous vehicle. The compositions may be in any physical form suitable for application to the hair and scalp or to other hairy body areas. Many such forms are known in the pharmaceutical and cosmetic arts and include, for example, liquids (e.g., liquid shampoos or hair rinses), aqueous gels or creams, lotions, and other conventional vehicles used for pharmaceutical and toiletry products applied to the hair or scalp. Liquid solutions of DMI (e.g., diluted with water) are also suitable for use in the invention.

In one preferred embodiment of the invention, the lice ova loosening composition is in the form of a thickened, aqueous gel comprising 1–50% DMI by weight, preferably about 5–25%; about 2–8% by weight of an organic acid such as acetic or citric acid; purified water; a thickening agent such as xanthan gum; and, optionally, softening, conditioning, fragrance and coloring agents. The gel composition may have a neutral pH (about 6–7), but preferably has a pH of about 2–5. The gel is preferably applied to the hair of a subject suffering from a louse infestation after the subject has been treated with a pediculicidal shampoo or rinse to kill the louse ectoparasites and at least some of the nits.

The gel composition may include, in addition to DMI, purified water and a thickener such as xanthan gum; conditioning agents, particularly silicone conditioners such as polydimethylsiloxane copolymers or silicone-polyether copolymers; emollients such as polyoxyalkyl stearyl ethers; an acid such as acetic, citric, formic, glycolic, lactic, malic, phosphoric or trichloroacetic acids to act as a pH modifier and, in some instances, as a preservative/stabilizer; emulsifiers; surfactants (preferably nonionic); and conventional fragrances and FDC approved coloring agents. The gel composition may be provided to consumers or health professionals in a jar, bottle, tube, individual dose packet, or any other container or dispensing modality known in the art.

In another preferred embodiment, the novel composition may comprise 1–50 percent DMI by weight in a conventional shampoo vehicle, with or without the presence of an active pediculicidal agent. Such shampoo vehicle may include, by way of example, deionized or purified water; detergents such as alkyl/aryl ether salts (e.g., Na+, Mg++, NH4+); thickeners such as cellulose derivatives and/or poly (ethylene oxide) ethers; antioxidants such as butylated hydroxytoluene; non-ionic coupling agents such as phenoxypolyethoxy ethanols; and suitable fragrance and coloring additives. In general, any shampoo vehicle which is compatible with DMI, is non-irritating and provides good foaming and rinsing action, is suitable for use in the subject shampoo compositions.

The subject compositions may also contain one or more active pediculicidal ingredients. By way of illustration, pyrethrins, preferably synergized pyrethrins, may be added to the compositions. Thus, the compositions might comprise pediculicidal and ovicidal shampoos such as the commercial product PRONTO® lice shampoo, marketed by Del Pharmaceuticals, Inc., (Uniondale, N.Y.), with sufficient DMI added to constitute 1–50%, and preferably 5–25%, by weight of the total composition. The PRONTO® shampoo includes pyrethrins synergized with piperonyl butoxide, together with a combination of a benzyl alcohol, a short chain aliphatic alcohol and a long chain aliphatic alcohol, the alcohol constituents serving to enhance the activity of the pyrethrin insecticide. It has been found that when sufficient DMI is added to a pediculicidal shampoo compositions to constitute from 1–50% by weight of the total, the compositions are active not only in killing the adults louse parasites and their ova but also in loosening and dislodging the ova from the hair shafts.

The compositions of the present invention may be prepared by any suitable means known in the cosmetic and pharmaceutical arts for producing hair gels or medicated shampoos. By way of example, the gel composition may be prepared by (a) mixing any emollients/solvents with the thickener/emulsifier at moderate heat (phase A), (b) mixing the DMI with purified water and surfactant with moderate heat (phase B), and then adding phase A to phase B and mixing while allowing the mixture to cool and form a homogeneous gel. Any conditioning, coloring and fragrance agents may be subsequently added and mixed into the gel.

The shampoo compositions may be prepared in several separate phases, with the subsequent gradual combination of the phases into a single batch which is mixed until a clear homogeneous liquid is achieved. These may comprise a first phase including, among other ingredients, the DMI, an alcohol (e.g., isopropyl alcohol) and surfactants; a second phase including the purified water; a third phase including detergents, conditioning agents and emulsifiers; and a fourth phase including one or more alcohols (e.g., isopropyl and benzyl) together with the pyrethrins, pyrethrin synergists and any preservatives and fragrances. The first three phases are each mixed separately until a homogeneous dispersion or solution is achieved, with the second phase then being mixed into the third phase, the fourth phase being added subsequently to the mixture and the first, DMI phase finally being added in small portions and mixed into the remaining phases until a homogeneous product is obtained, The above methods of preparation are merely illustrative. Any of the many techniques and production methods known in the art of formulating hair and scalp treatment products may be utilized to prepare the subject compositions.

The compositions of the invention are not limited to the preferred embodiments of a thickened, aqueous gel and a shampoo. The DMI-containing, lice ova loosening or removing compositions can take the form of a cream rinse applied to the hair following the application of a pediculicidal product to condition the hair while loosening and dislodging the nits from the hair shafts. Any other conventional vehicle safe and gentle enough for application to the hair and scalp and compatible with DMI may be used.

The invention also comprehends a method of treating a human subject suffering from an infestation of lice in a hairy area, particularly in the scalp area, to loosen, dislodge and/or remove the lice ova attached by the adult parasites (ectoparasites) to the hair shafts. The method of treatment comprises the application of an effective lice ova-loosening amount of the DMI-containing compositions described above to the hairy area, and then removing the composition from the area after a suitable period of time, preferably by rinsing out with water. Any remaining nits may be removed by fine-tooth combing, tweezers or other mechanical means after the hair is towel-dried.

The invention also comprehends a method of treating a human subject suffering from an infestation of lice in a hairy area, particularly in the hair and scalp area, to simultaneously (i) kill adult parasites and their ova, and (ii) loosen, dislodge and/or remove the lice ova attached to the hair shafts. The method of providing this combined treatment comprises the application of an effective lice ova-loosening amount of a composition according to the invention which contains not only DMI, but also an active pediculicidal/ovicidal ingredient. An example of such composition would be a shampoo containing both DMI and pyrethrins.

The term "hairy areas" may refer to the subject's scalp, pubic area, underarms, chest or any other hirsute area of the body where louse infestations typically occur. The louse species whose infestations may be treated by the methods of the invention include not merely head lice, but also, by way of illustration, crab lice (*Phthirus pubis*), body lice (*Pediculus humanus corporis*) and their nits.

The nit-loosening effectiveness of the novel compositions and the methods of treatment employing them were tested extensively using an INSTRON® 1123 Universal Testing Instrument (Instron Corp. Canton, Mass.). This instrument, in conjunction with a CORREX® Gram Gage (SPI, Switzerland), measures the force required to loosen nits from a hair shaft and records it on paper. The compositions of the invention were found to be highly effective in decreasing the force required to remove nits with a fine tooth comb from hair shafts, more effective than commercially available prior art products marketed for the same purpose.

In a further aspect of the present invention, lice ova removal kits are provided. These kits contain at least one treatment amount of at least one composition according to the invention, one or more plastic or metal nit removal combs and, optionally, an instruction guide (on the kit package or inserted therein) for practicing the lice ova removal method of the invention.

The following are specific illustrative examples of compositions in accordance with the present invention, methods of preparing the same and methods of treatment employing these compositions. Testing methods and data are also set forth to illustrate the surprising effectiveness of the invention in facilitating louse ova removal from the hair. These examples are not intended to limit or restrict the scope of the invention in any way and should not be construed as identifying specific materials, concentration ranges, methods of preparation or methods of treatment which must be utilized exclusively in order to practice the present invention.

EXAMPLE 1

DMI-Containing Gels

The following gel compositions were prepared:

FORMULA A:

| | | Ingredients | % w/w | g/300 g |
|---|---|---|---|---|
| A | 1 | Purified water | 50.0 | 150.0 |
| | 2 | Xanthan gum | 0.7 | 2.1 |

-continued

FORMULA A:

| | | Ingredients | % w/w | g/300 g |
|---|---|---|---|---|
| | 3 | Silsoft ® 148[1] | 2.0 | 6.0 |
| | 4 | Silsoft ® A-843[2] | 1.5 | 4.5 |
| B | 1 | Purified water | 15.8 | 47.4 |
| | 2 | Acetic acid | 5.0 | 15.0 |
| | 3 | Dimethyl isosorbide | 25.0 | 75.0 |

[1]Aminomodified silicone polyethere copolymer (Witco Corp., Organo Silicones Group).
[2]Polydimethylsiloxane/polydimethylsiloxane cyclic pentamer blend (Witco Corp., Organo Silicones Group).

FORMULA B:

| | | Ingredients | % w/w | g/300 g |
|---|---|---|---|---|
| A | 1 | Purified water | 50.0 | 150.0 |
| | 2 | Xanthan gum | 0.6 | 1.8 |
| | 3 | Silsoft ® 148 | 2.0 | 6.0 |
| | 4 | Silsoft ® A-843 | 1.5 | 4.5 |
| B | 1 | Purified water | 17.9 | 53.7 |
| | 2 | Citric acid | 3.0 | 9.0 |
| | 3 | Dimethyl isosorbide | 25.0 | 75.0 |

FORMULA C:

| | | Ingredients | % w/w | g/300 g |
|---|---|---|---|---|
| A | 1 | Purified water | 53.2 | 159.6 |
| | 2 | Xanthan gum | 0.5 | 1.5 |
| | 3 | Silsoft ® 148 | 2.0 | 6.0 |
| | 4 | Silsoft ® A-843 | 1.5 | 4.5 |
| B | 1 | Dimethyl isosorbide | 39.8 | 119.4 |
| | 2 | Salicylic acid | 3.0 | 9.0 |

(Formulas A–C):

A. Sprinkle A2 into vortex of A1 and mix for 20 minutes. Add A3 and A4 and mix for 10 minutes.

B. Add B2 into B1 and mix until dissolved. Add B3 and mix until uniform. Add phase B into phase A and mix for 10 minutes.

FORMULA D:

| | | Ingredients | % w/w | g/150 g |
|---|---|---|---|---|
| A | 1 | Dimethyl isosorbide | 10.00 | 15.0 |
| | 2 | Xanthan gum (Keltrol) | 0.70 | 1.05 |
| | 3 | Purified Water USP | 78.30 | 117.45 |
| | 4 | Glacial acetic acid USP | 5.00 | 7.5 |
| | 5 | Procetyl AWS[5] | 2.00 | 3.0 |
| | 6 | Silsoft ® 148 | 2.00 | 3.0 |
| | 7 | Silsoft ® 843 | 1.50 | 2.25 |
| | 8 | Kiwi fragrance J9623E | 0.50 | 0.75 |

[5]Polypropylene glycol-5-ceteth-20 (Croda International).

FORMULA E:

| | | Ingredients | % w/w | g/150 g |
|---|---|---|---|---|
| A | 1 | Dimethyl isosorbide | 25.00 | 37.50 |
| | 2 | Xanthan gum (Keltrol) | 0.70 | 1.05 |
| | 3 | Purified Water USP | 63.30 | 94.95 |
| | 4 | Glacial acetic acid USP | 5.0 | 7.50 |
| | 5 | Procetyl AWS | 2.00 | 3.00 |
| | 6 | Silsoft ® 148 | 2.00 | 3.00 |
| | 7 | Silsoft ® 843 | 1.50 | 2.25 |
| | 8 | Kiwi fragrance J9623E | 0.50 | 0.75 |

Procedures (Formulas D–E):

Add A1 into a beaker; add A2 into A1 and mix for 15 minutes.

Add A3 and mix for 45 minutes.

Add A4 and mix for 10 minutes.

Add A5 and mix for 5 minutes.

Add A6 and mix for 5 minutes.

Add A7 and mix for 5 minutes.

Add A8 and mix for 20 minutes.

EXAMPLE 2

DMI-Containing Pediculicidal/Ovicidal Shampoo Compositions

The following liquid shampoo compositions were prepared:

FORMULA F:

| | | Ingredients | % w/w | g/150 g |
|---|---|---|---|---|
| A | 1 | Dimethyl isosorbide | 5.0 | 7.5 |
| | 2 | Isopropyl alcohol | 15.0 | 22.5 |
| | 3 | Polyox[6] ® WSRN 3000 | 0.375 | 0.563 |
| | 4 | Polyox WSR 205 | 0.375 | 0.563 |
| B | 1 | Purified Water | 17.748 | 26.622 |
| | 2 | Hampene[7] Na$_2$ | 0.1 | 0.15 |
| C | 1 | Poloxamer 183 | 5.0 | 7.5 |
| | 2 | Glycerin, 96% | 5.0 | 7.5 |
| | 3 | Ammonium laureth sulfate | 27.0 | 40.5 |
| D | 1 | Isopropyl alcohol | 10.0 | 15.0 |
| | 2 | Benzyl benzoate | 2.5 | 3.75 |
| | 3 | Butylated hydroxytoluene | 0.2 | 0.3 |
| | 4 | Benzyl alcohol | 5.0 | 7.5 |
| | 5 | Shampoo fragrance J-9181 | 1.0 | 1.5 |
| | 6 | Premium Pyrocide ®[8] | 1.702 | 2.552 |
| | 7 | Piperonyl butoxide | 4.0 | 6.0 |

[6]Poly(ethylene oxide) (Union Carbide, Danbury, CT)
[7]Ethylenediaminetetracetic acid, sodium salt (Hampshire Chemical Corp., Lexington, MA)
[8]Pyrethrins petroleum distillate (McLaughlin Gormley King, Minneapolis, MN)

FORMULA G:

| | | Ingredients | % w/w | g/150 g |
|---|---|---|---|---|
| A | 1 | Dimethyl isosorbide | 10.0 | 7.5 |
| | 2 | Isopropyl alcohol | 10.0 | 22.5 |
| | 3 | Polyox ® WSRN 3000 | 0.375 | 0.563 |
| | 4 | Polyox WSR 205 | 0.375 | 0.563 |
| B | 1 | Purified Water | 17.748 | 26.622 |
| | 2 | Hampene Na$_2$ | 0.1 | 0.15 |
| C | 1 | Poloxamer 183 | 5.0 | 7.5 |
| | 2 | Glycerin, 96% | 5.0 | 7.5 |
| | 3 | Ammonium laureth sulfate | 27.0 | 40.5 |
| D | 1 | Isopropyl alcohol | 10.0 | 15.0 |
| | 2 | Benzyl benzoate | 2.5 | 3.75 |
| | 3 | Butylated hydroxytoluene | 0.2 | 0.3 |
| | 4 | Benzyl alcohol | 5.0 | 7.5 |
| | 5 | Shampoo fragrance J-9181 | 1.0 | 1.5 |
| | 6 | Premium Pyrocide ® | 1.702 | 2.552 |
| | 7 | Piperonyl butoxide | 4.0 | 6.0 |

Procedure

A. Add A3 and A4 into A2 and mix for 15 minutes (form slurry). Add A1 to slurry while mixing.

B. Add B2 into B1 and mix until clear (15 minutes). Add phase A into phase B and mix for one hour (to completely hydrate the polyox resins).

C. Add C1 through C3 individually into phase A/B while mixing. Mix for 30 minutes.

D. Add D2 through D7 into D1, mix for 30 minutes. Add phase D into main batch. Mix for 30 minutes.

EXAMPLE 3

Laboratory tests were performed to measure the decrease in the combing force required to remove nits from hair strands treated with various compositions of the invention as compared with controls and with prior art egg-loosening compositions. The test apparatus, described below, is shown in FIGS. 1 and 2.

Figure 2:
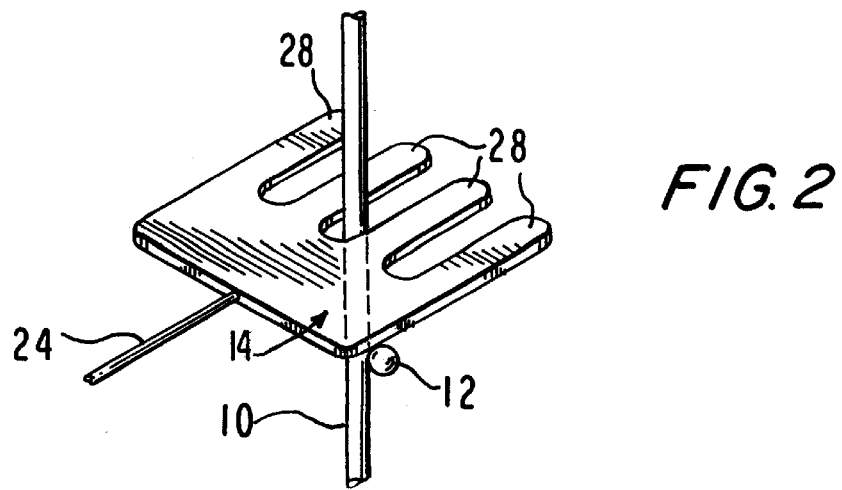
FIG. 2 is a view showing the positioning of the nit and hair strand between the teeth of the comb shown in the test setup of FIG. 1.

Test Materials (FIG. 1)

1. Hair strand 10 with nit 12 attached.
2. Fine tooth plastic nit comb 14.
3. Controls and test compositions.
4. INSTRON® 1123 Universal Testing Instrument 16 (Instron Corp., Canton, Mass.) with a 0–50 kg load cell 18.
5. CORREX® Gram Gage 20—2–15 g with flat tip (SPI, Switzerland).
6. Clamp plate assembly 22.
7. Iron support 24 with clamp 26 for holding the Correx Gram Gage 20.

Testing Procedure a) Set up the Instron 16 for test of loosening nits from hair strand.
   Set "Crosshead Speed" at 1.0 mm/min.
   Set "Load Cell Amplifier" at 0.1 (i.e., one small square represents 1.0 g in the Chart).
   Set "Chart Drive Speed" at 5.0 mm/min.

b) Fix the nit comb 14 to the flat tip of Correx Gram Gage 20 which is held by the iron support 24, and dial the needle of the Gage to "Zero point".

c) Set up the specimens: The hair strand 10 with a nit 12, which has been treated with the control or test compositions, is clamped in the clamp plate assembly 22 with the nit bottom up, and hang the assembly on the hook 26 of load cell 18.

d) Set the hair strand 10 between the teeth 28 of the nit comb 14, with the nit 12 immediately below the teeth (see FIG. 2).

e) Start the Instron, and the force required to loosen the nits will be recorded by the paper chart recorder 30, and can also be read on the Gram Gage 20.

Results

Tables 1 through 4 reflect the data generated through the above testing procedure as applied to untreated hair strands and strands treated respectively with (i) various DMI-containing compositions of the invention, (ii) commercially available lice egg removing compositions and (iii) controls including warm water and a solution of citric acid in water.

The data are expressed in terms of the grams of force required for the comb to dislodge the nit from the hair strand.

TABLE 1

|  | Hair Samples | Hair Samples Treated with Nit Loosening Products (force in g) | | | | |
| --- | --- | --- | --- | --- | --- | --- |
| Hair Samples with Nits | treated with Warm Water | Gel Formula A | Gel Formula B | Gel Formula C | Pronto ® Creme Rinse[8] | Clear ® Lice Egg Remover[9] |
| 1 | 5.50 | 4.00 | 2.25 | 9.00 | 5.00 | 2.75 |
| 2 | 4.00 | 6.00 | 6.00 | 4.00 | 5.75 | 4.00 |
| 3 | 5.00 | 4.25 | 4.25 | 7.00 | 2.25 | 5.00 |
| 4 | 10.00 | 1.25 | 3.00 | 10.75 | 5.00 | 4.00 |
| 5 | 4.50 | 4.50 | 7.75 | 7.50 | 4.00 | 9.25 |
| 6 | 5.00 | 5.00 | 2.50 | 2.50 | 3.80 | 9.50 |
| 7 | 4.25 | 5.00 | 7.75 | 6.50 | 1.50 | 7.00 |
| 8 | 7.00 | 3.50 | 4.00 | 10.00 | 7.00 | 3.00 |
| 9 | 8.00 | 3.50 | 5.00 | 8.00 | 5.00 | 4.00 |
| 10 | 8.00 | 2.00 | 8.00 | 5.20 | 4.75 | 8.50 |
| 11 | 5.00 | 2.50 | 3.50 | 5.25 | 4.80 | 5.00 |
| 12 | 8.25 | 4.00 | 3.50 | 6.00 | 7.00 | 8.00 |
| 13 | 3.00 | 1.50 | 7.00 | 6.75 | 7.50 | 4.00 |
| 14 | 6.00 | 2.50 | 3.00 | 7.00 | 3.50 | 5.00 |
| 15 | 5.50 | 3.00 | 6.00 | 6.50 | 2.50 | 2.25 |
| 16 | 2.50 | 3.00 | 3.00 | 9.50 | 3.50 | 6.00 |
| 17 | 4.50 | 3.50 | 2.50 | 8.25 | 6.20 | 5.00 |
| 18 | 10.50 | 2.00 | 3.50 | 4.00 | 7.50 | 11.50 |
| 19 | 7.50 | 2.20 | 3.25 | 5.00 | 5.80 | 3.75 |
| 20 | 2.50 | 2.75 | 2.50 | 3.00 | 4.50 | 11.00 |
| x ± σ | 5.82 ± 2.30 | 3.29 ± 1.26 | 4.41 ± 1.95 | 6.58 ± 2.28 | 4.84 ± 1.71 | 5.92 ± 2.79 |
| P Value vs. samples treated with warm water |  | <0.001 | <0.05 (p = 0.043) |  | no significance (p = 0.301) | no significance (p = 0.134) no significance (p = 0.92) |

TABLE 2

|  |  | Hair Samples Treated with (force in g) | | |
| --- | --- | --- | --- | --- |
| Hair Samples with Nits | Hair Samples Untreated (g) | Solvent (50% DMI w/w) | Citric Acid, 15% (W/V) (pH = 1.3) | Warm Water |
| 1 | 9.0 | 2.0 | 4.0 | 6.5 |
| 2 | 6.0 | 4.0 | 2.0 | 5.0 |
| 3 | 10.0 | 5.0 | 6.0 | 4.5 |
| 4 | 7.0 | 3.0 | 2.0 | 7.0 |
| 5 | 7.5 | 6.0 | 2.0 | 5.0 |
| 6 | 6.5 | 3.5 | 3.5 | 5.0 |
| 7 | 7.0 | 2.5 | 1.5 | 10.5 |
| 8 | 8.5 | 4.0 | 3.5 | 5.0 |
| 9 | 10.5 | 2.0 | 2.5 | 6.0 |
| 10 | 9.5 | 2.5 | 2.5 | 5.0 |
| 11 | 15.0 | 4.5 | 7.5 | 3.5 |
| 12 | 5.0 | 5.0 | 4.5 | 8.5 |
| 13 | 11.0 | 6.0 | 3.5 | 3.5 |
| 14 | 7.5 | 2.5 | 2.5 | 5.0 |
| 15 | 6.5 | 3.0 | 2.0 | 7.0 |
| x ± σ | 8.43 ± 2.52 | 3.70 ± 1.36 | 3.30 ± 1.66 | 5.80 ± 1.86 |
| P Value vs. untreated samples |  | <0.001 | <0.001 | <0.05 |
| vs. treated with warm water |  | <0.005 | <0.001 |  |

TABLE 3

Hair Samples Treated with Nit Loosening Products (force in g)

| Hair Samples with Nits | Hair Samples* Treated with Warm Water | RID ® Lice Egg Loosener Gel[10] (ph = 6.17) | Clear ® Lice Egg Remover (ph = 4.97) | Shampoo Formula F (5% DMI) | Shampoo Formula G (10% DMI) |
|---|---|---|---|---|---|
| 1 | 6.00 | 6.00 | 3.00 | 2.50 | 6.50 |
| 2 | 7.00 | 5.50 | 7.00 | 3.50 | 1.75 |
| 3 | 5.00 | 3.00 | 6.00 | 5.50 | 4.00 |
| 4 | 4.00 | 5.00 | 8.00 | 3.00 | 2.00 |
| 5 | 5.50 | 6.00 | 5.50 | 3.00 | 2.00 |
| 6 | 7.00 | 7.00 | 12.50 | 6.50 | 2.50 |
| 7 | 12.00 | 12.00 | 6.00 | 3.50 | 2.00 |
| 8 | 6.00 | 8.00 | 7.00 | 3.00 | 1.00 |
| 9 | 8.00 | 4.75 | 11.00 | 5.50 | 6.00 |
| 10 | 7.00 | 5.00 | 6.00 | 6.00 | 3.50 |
| 11 | 6.50 | 6.50 | 5.50 | 7.00 | 4.00 |
| 12 | 7.00 | 4.50 | 8.00 | 6.50 | 1.00 |
| 13 | 4.00 | 9.50 | 4.00 | 6.50 | 4.00 |
| 14 | 6.00 | 7.00 | 8.00 | 5.00 | 3.50 |
| 15 | 6.50 | 8.00 | 4.50 | 5.50 | 2.00 |
| 16 | 6.00 | 8.00 | 7.00 | 4.50 | 2.00 |
| 17 | 5.00 | 8.00 | 4.00 | 4.00 | 1.00 |
| 18 | 6.00 | 6.00 | 6.00 | 4.00 | 2.50 |
| 19 | 11.00 | 9.00 | 6.00 | 3.50 | 4.50 |
| 20 | 12.00 | 11.00 | 5.50 | 4.00 | 2.00 |
| $x \pm \sigma$ | 6.87 ± 2.29 | 6.98 ± 2.24 | 6.52 ± 2.25 | 4.62 ± 1.41 | 2.88 ± 1.57 |
| P Value vs. samples treated with warm water | | no significance (P = 0.877) | no significance (P = 0.630) | <0.001 | <0.001 |
| P Value vs. samples treated | | | with 5% DMI Pronto Shampoo <0.005 (P = 0.003) | with 10% DMI Pronto Shampoo <0.001 | with Clear Lice Egg Remover <0.001 |

*Hair samples treated with warm water were used as the negative control.

TABLE 4

| | Hair Samples Treated with (force in g) | | |
|---|---|---|---|
| Hair Samples with Nits | Hair Samples Treated with Warm Water | Gel Formula D (10% DMI, 5% acetic acid, ph~3) | Gel Formula E (25% DMI, 5% acetic acid, ph~3) |
| 1 | 4.00 | 3.00 | 2.00 |
| 2 | 8.50 | 2.50 | 2.00 |
| 3 | 6.50 | 4.50 | 2.50 |
| 4 | 10.50 | 4.50 | 4.50 |
| 5 | 5.00 | 4.00 | 5.00 |
| 6 | 6.00 | 4.00 | 3.50 |
| 7 | 5.50 | 1.50 | 3.00 |
| 8 | 11.00 | 4.00 | 2.00 |
| 9 | 8.50 | 1.50 | 4.00 |
| 10 | 11.00 | 4.50 | 4.00 |
| 11 | 4.50 | 2.00 | 3.00 |
| 12 | 7.00 | 1.50 | 3.00 |
| 13 | 4.00 | 3.50 | 3.00 |
| 14 | 8.50 | 4.00 | 2.50 |
| 15 | 4.00 | 5.00 | 3.00 |
| 16 | 8.50 | 2.00 | 4.00 |
| 17 | 8.00 | 4.00 | 4.50 |
| 18 | 6.50 | 2.00 | 1.50 |
| 19 | 6.00 | 2.50 | 2.50 |
| 20 | 5.50 | 4.00 | 3.50 |
| $\chi \pm \sigma$ | 6.95 ± 2.27 | 3.22 ± 1.17 | 3.15 ± 0.96 |
| P Value vs. samples treated with warm water | | <0.001 | <0.001 |

The DMI-containing compositions of the present invention are easy and inexpensive to formulate and produce in commercial quantities. They exhibit low toxicity and are safe and pleasant to use. By providing substantially increased lice ova loosening activity in comparison with prior art compositions, the compositions of the invention can reduce the frequency and duration of treatments for louse infestation by ensuring that fewer eggs remain in the hair after each pediculicidal/ovicidal treatment.

It will thus be seen that there are provided compositions which achieve the various objects of the invention and which are well adapted to meet the conditions of practical use. As various possible embodiments might be made in the embodiments set forth above, it is to be understood that all matters herein described are to be interpreted as illustrative and not in a limiting sense.

What is claimed as new and desired to be protected by letters patent is set forth in the appended claims.

We claim:

1. A topical gel composition for loosening or dislodging lice ova from the hair of a human subject, comprising in an aqueous gel vehicle (a) about 5–25% dimethylisosorbide (DMI) by weight of the total composition, and (b) an acid selected from the group consisting of acetic, citric, lactic, malic, phosphoric and trichloroacetic acids, said composition having a pH of about 2–5.

2. A gel composition according to claim 1 which additionally comprises purified water and a thickening agent.

3. A gel composition according to claim 1 which additionally comprises a conditioning agent, an emollient, an emulsifier or a surfactant.

4. A gel composition according to claim 2 wherein the thickening agent is xanthan gum.

5. A gel composition according to claim 1 which comprises about 2–8% by weight of said acid.

6. A gel composition according to claim 1 wherein said acid is acetic acid.

7. A gel composition according to claim 6 which contains about 5% by weight of acetic acid.

8. A gel composition according to claim 1 comprising about 5% DMI by weight.

9. A gel composition according to claim 1 comprising about 10% DMI by weight.

10. A gel composition according to claim 1 comprising about 25% DMI by weight.

\* \* \* \* \*